US006781686B2

(12) United States Patent
Hunt

(10) Patent No.: US 6,781,686 B2
(45) Date of Patent: Aug. 24, 2004

(54) FEMTOSECOND OPTICAL SURFACE IMAGING

(75) Inventor: Jeffrey H. Hunt, Chatsworth, CA (US)

(73) Assignee: The Boeing Company, Chicago, IL (US)

( * ) Notice: Subject to any disclaimer, the term of this patent is extended or adjusted under 35 U.S.C. 154(b) by 121 days.

(21) Appl. No.: 10/175,470

(22) Filed: Jun. 19, 2002

(65) Prior Publication Data

US 2003/0234927 A1 Dec. 25, 2003

(51) Int. Cl.[7] ............................................. G01N 21/88
(52) U.S. Cl. .................. 356/237.2; 356/309; 250/559.4
(58) Field of Search ................ 356/237.1, 237.2–237.5, 356/309, 317–334, 73; 250/559.4, 559.41

(56) References Cited

U.S. PATENT DOCUMENTS

| | | |
|---|---|---|
| 5,294,289 A | 3/1994 | Heinz et al. |
| 5,623,341 A | 4/1997 | Hunt |
| 5,875,029 A | 2/1999 | Jann et al. |
| 5,883,714 A | 3/1999 | Jann et al. |
| 5,898,499 A | 4/1999 | Pressesky |
| 5,923,423 A | 7/1999 | Sawatari et al. |
| 5,973,778 A | 10/1999 | Hunt |
| 6,317,514 B1 | 11/2001 | Reinhorn et al. |
| 6,359,451 B1 | 3/2002 | Wallmark |

OTHER PUBLICATIONS

"Light Waves at the Boundary of Nonlinear Media"—The Physical Review, 128, p. 193, 1962, Bloembergen and P.S. Pershan.
"Surface Studies by Optical Second Harmonic Generation: an Overview"—Journal of Vacuum Science and Technology B, vol. 3, No. 5, Sep. Oct. 1985, pp. 1464–1466, Y.R. Shen.

Primary Examiner—Richard A. Rosenberger
Assistant Examiner—Vincent P. Barth
(74) Attorney, Agent, or Firm—Shimokaji & Associates, P.C.

(57) ABSTRACT

Two laser inputs having pulse durations of about 50–100 femtoseconds are directed to an area of a surface to be interrogated. The lasers are aligned so that their surface areas of optical illumination overlap on the interrogated surface. An optical delay line temporarily synchronizes the two inputs. An output wavelength discriminator receives reflections of the inputs from the interrogated surface and is substantially non-transmissive at the frequencies of the first laser input and the second laser input, but is substantially transmissive at the sum-frequency of the first input and the second input. Imaging optics direct the propagation of the output so that a real image is formed. A position sensitive detector monitors the intensity of the real image at the sum-frequency and an electronic signal equivalent to the real image is provided. The femtosecond duration laser inputs generate enhanced peak optical powers on the interrogated surface, producing an optimized sum-frequency reflection, resulting in minimized interrogation times.

29 Claims, 1 Drawing Sheet

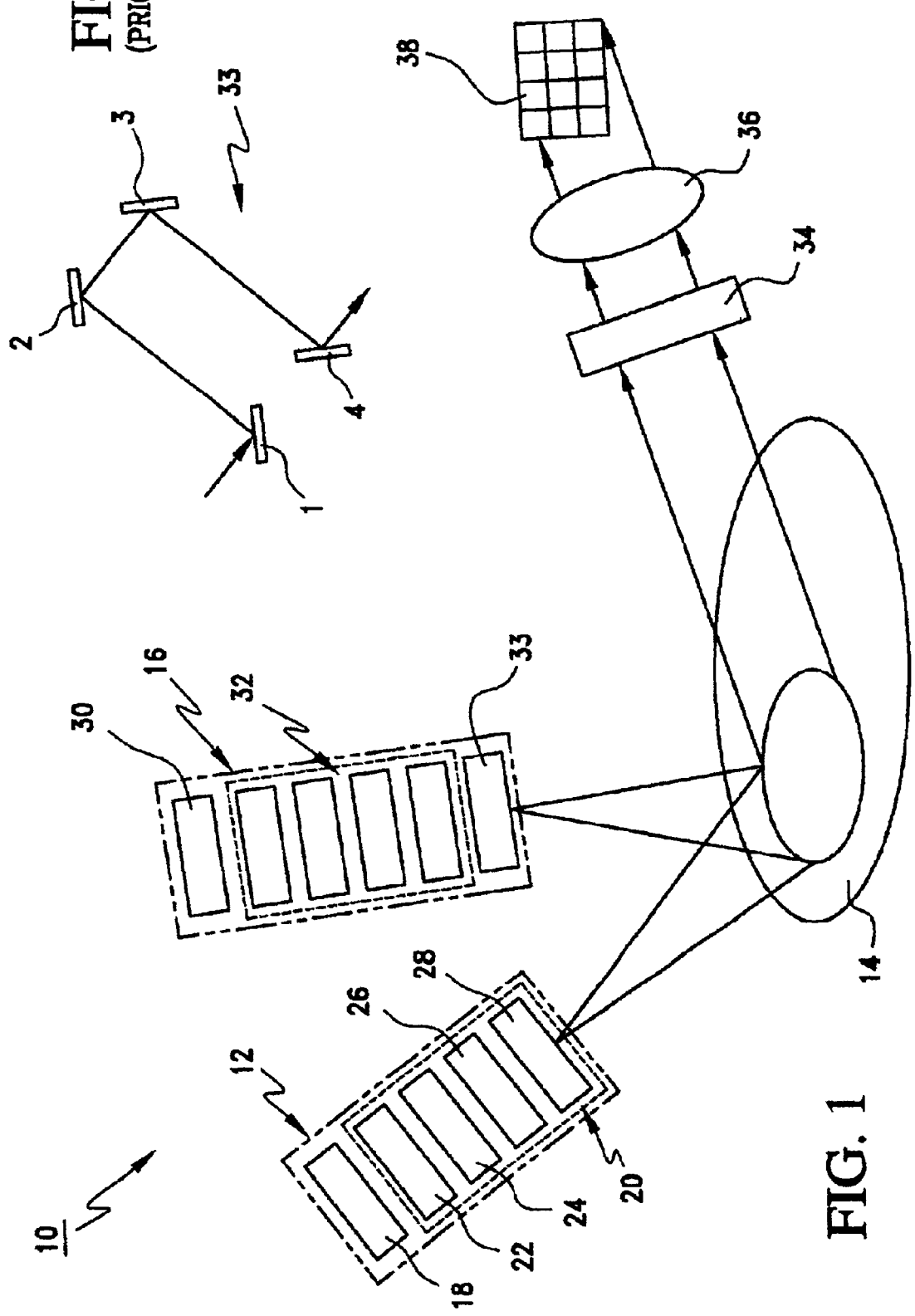

FEMTOSECOND OPTICAL SURFACE IMAGING

BACKGROUND OF THE INVENTION

1. Field of the Invention

The present invention relates to monitoring the properties of a surface and more particularly to the use of second-order nonlinear optics to generate a surface specific position sensitive image of contaminants that are present on the surface

2. Description of the Related Art

In the most general sense, the term "surface" applies to any interface between two media. It is not restricted by the material phase of matter and can be between a gas and a solid, a gas and a liquid, between two liquids, between a solid and a liquid, between two solids, etc.

In the study and characterization of surfaces or interfacial media, it is important to create an image or map of the interface which correlates a property to a location on the surface. Depending on the application, chemical, mechanical or molecular properties may need to be monitored on a surface. Additionally, the properties of a location or locations on a surface need to be monitored simultaneously. This monitor should be nonintrusive, noninvasive and should not be restricted in use by the ambient environment which surrounds it. Consequently, one usually uses optical sensing, as light propagation is not restricted by ambient environment, so long as the environment is transparent to the light. Unfortunately, linear optical diagnostics, i.e., those in which the output frequency is the same as the input, are not surface specific. Output signals will include large contributions from the bulk, so that subtle changes on the surface will only weakly affect the output signal.

There are many techniques which can be used to analyze molecular properties or behavioral properties at an interface. Unfortunately, the vast majority of them have rather severe environmental limitations on their application. Many of them are restricted to ultra-high vacuum, with the implication that any liquid or liquid/solid interface may not be tested. Even if one wanted to inspect a vacuum-solid interface, one would have to take the material to be examined and place it in a high vacuum chamber. This can often be slow, expensive or impossible depending on the size of the particular material in question.

Other surface diagnostic techniques require that the interface be inserted into other environments, such as the interface between two solids, in which case it may be necessary to destroy the particular material to be studied. Still, other techniques require either fabrication of very exotic detection means or require signal integration times which makes them unusable in any sort of real time industrial scenario.

Discussed herein are NLO techniques to solve pragmatic problems that occur in industry. For example, materials processing, surface contamination, surface corrosion, etc. are problems that are addressed. In nonlinear optics, outputs are produced at sum, difference or harmonic frequencies of the input(s). Using second order nonlinear optical surface spectroscopy to examine the physical properties and behavior of a surface or interface was originally proposed in the 1960's in "Light Waves at the Boundary of Nonlinear Media" by Bloembergen and P. S. Pershan, The Physical Review, 128, Page 193 (1962). Experimental work involving second harmonic generation was also performed. However, because lasers at the time were comparatively feeble, impractical, slow, etc., there was little subsequent work done on the development of second harmonic generation or, more generally, second order nonlinear optical (NLO) processes at surfaces until considerably later when high peak power lasers became reliable and commercially available.

Recently, researchers have reviewed NLO processing and concluded that lasers had developed enough that they could be used for studying the physical and chemical properties of surfaces and interfaces. For example, a theoretical study of the physics of the interface, and not its engineering aspects, has been performed. See Journal of Vacuum Science and Technology B, Volume 3, Number 5, September October 1985, Pages 1464–1466, Y. R. Shen, "Surface Studies by Optical Second Harmonic Generation: an Overview."

In U.S. Pat. No. 5,294,289, T. F. Heinz et al. discuss the use of second harmonic generation as a means to monitor the epitaxial growth of silicon semiconductor structures in a high vacuum chamber. Specifically, they examined the spectroscopic response at the interface between the electronically active silicon and the insulative layer of calcium. By monitoring the magnitude of the resonance, they could ascertain whether the insulator was present on the surface and whether it had electronically binged to the underlying semiconductor. The system that is used only examines the total intensity of the light that is collected and there is no attempt to associate position sensitive information with the second harmonic. There is also no discussion of the use of second harmonic generation (SHG) for the detection of contamination. In addition, the preferred embodiment only discusses an optical system which employs nanosecond duration pulses.

In U.S. Pat. No. 5,623,341, J. H. Hunt discusses the use of sum-frequency generation for the detection of contamination and corrosion on engine parts. In this incarnation, one of the inputs is a tunable IR beam that is tuned to a resonance of the contamination on the surface. The efficiency of the sum-frequency process is increased (so-called resonant enhancement) when the IR beam is resonant with a contaminant. If the contaminant is not present, there is no resonant enhancement. By comparing on and off resonant signals, the presence and level of contaminant can be deduced. However, there is no attempt to associate position sensitive information with the sum-frequency signal and there is no discussion of the use of laser pulses with femtosecond durations.

In U.S. Pat. No. 5,875,029, P. C. Jann et al. describe a versatile optical inspection instrument and method to inspect magnetic disk surfaces for surface defects. The device provides surface position information of the defects. However, the technique involves only linear optical processes. That is, the input and output light wavelengths are the same.

In U.S. Pat. No. 5,883,714, Jann et al. describe a versatile optical inspection instrument and method to inspect magnetic disk surfaces for surface defects. The device is based on interferometric measurement and detects contaminants by measuring the Doppler shift in the light that results from scanning the light onto a contaminant or defect. By scanning, the device provides surface position information of the defects. However, the technique involves only linear optical processes and senses only phase changes. That is, the input and output light wavelengths are the same.

In U.S. Pat. No. 5,898,499, J. L. Pressesky discusses a system for detecting local surface discontinuities in magnetic storage discs. The device is an interferometric detector which scans the disc in a spiral motion. Local defects cause local changes in phase which are measured by interferometric techniques. This is a linear optical technique.

In U.S. Pat. No. 5,932,423, T. Sawatari et al. discuss a scafterometer for detecting surface defects in semiconductor wafers. This device is a linear interferometric device.

In U.S. Pat. No. 5,973,778, J. H. Hunt discusses the use of second harmonic generation for investigating molecular alignment within a thin polyimide film. The technique uses changes in the second harmonic polarization to determine surface molecular alignment. There is no discussion of semiconductor materials or contamination and there is no attempt to associate position sensitive information with the second-harmonic signal and there is no discussion of the use of femtosecond pulses.

In U.S. Pat. No. 6,317,514 B1, S. Reinhorn et al. discuss a method and apparatus for inspecting a wafer surface to detect the presence of conductive material on the wafer. The device uses UV initiated electron emission to determine the location of conductive areas. Those areas which are metal will emit electrons. If the area which is supposed to be conductive is not, there will be no electron emission.

In U.S. Pat. No. 6,359,451 B1, G. N. Wallmark discusses a system for testing for opens and shorts between conductor traces on a circuit board. The technique uses electron scattering to perform its diagnostics and has no optics associated with it.

SUMMARY

In a broad aspect, the surface specific optical diagnostic system includes a first optical source for providing a first laser input directable to an area of a surface to be interrogated. The first laser input has a pulse having a duration of about 50–100 femtoseconds. A second optical source provides a second laser input directable to that surface area. The second laser input also has a pulse having a duration of about 50–100 femtoseconds. These lasers are alignable so that their surface areas of optical illumination overlap on the interrogated surface. The second optical source includes an optical delay line for temporarily synchronizing the first and second laser inputs. An output wavelength discriminator receives reflections of the first and second laser inputs from the interrogated surface. The output wavelength discriminator is substantially non-transmissive at the frequencies of the first laser input and the second laser input, but is substantially transmissive at the sum-frequency of the first laser input and the second laser input. Imaging optics receive an output of the wavelength discriminator and direct the propagation of the output so that a real image is formed after propagation through the imaging optics. A position sensitive detector monitors the intensity of the real image at the sum-frequency so that the sum-frequency, as a function of surface position, is converted to an electronic signal equivalent to the real image. Utilization of the femtosecond duration laser inputs generates enhanced peak optical powers on the interrogated surface, producing an optimized sum-frequency reflection, resulting in minimized interrogation times.

Active imaging, in which one directs a laser at an object and collects the returned light, has been used to create optical representations of targets for some time. Optical techniques have certain advantages over other sensing devices in that they are not restricted by environment and can be used in a remote configuration. Second order nonlinear optical techniques have been used to perform surface sensitive diagnostics, but to the present, have only been used on a point by point examination. These nonlinear optical effects are coherent. That is, the light that is generated by them travels in a well-defined matter, akin to a specular linear reflection. Consequently, it is possible to perform active imaging of a surface, exploiting the nonlinear optical response of the surface. This provides a means to do surface sensitive imaging while maintaining the advantages of an optical technique. When the basic development work was being performed, the laser systems which were employed were typically of nanosecond duration. This duration was not due to system optimization, but was merely based on the lasers that were available at the time. Work performed in these experiments showed that shorter pulses allowed higher peak intensities without causing surface modifications or damage. In order to produce an image, much of the optical intensity is distributed over the area to be imaged, reducing the peak intensity. The incorporation of femtosecond pulses increases the peak intensity to levels which allow for the rapid acquisition of image data.

Other objects, advantages, and novel features will become apparent from the following detailed description of the invention when considered in conjunction with the accompanying drawings.

BRIEF DESCRIPTION OF THE DRAWING

FIG. 1 is a schematic representation of the diagnostic system of the present invention.

FIG. 2 (Prior Art) is a schematic representation of an optical delay line utilized by the present invention.

DETAILED DESCRIPTION OF THE INVENTION

Referring now to the drawings and the characters of reference marked thereon, FIG. 1 illustrates a preferred embodiment of the diagnostic system of the present invention, designated generally as 10. Diagnostic system 10 includes a first optical source, indicated by phantom lines 12 for providing a first laser input that is directable to an area of a surface 14 to be interrogated. A second optical source 16 provides a second laser input that is also directable to the surface area to be interrogated. The optical sources 12, 16 are aligned so that their surface areas of optical illumination overlap on the interrogated surface 14. This alignment may be implemented via a series of refractive and reflective elements. For example, by changing their tilt in two axes, two mirrors in series can propagate a laser beam to any position on a surface.

The first optical source 12 includes a laser input 18 in optical communication with an associated input optics 20. The laser 18 has a pulse duration of about 50–100 femtoseconds, preferably in a range of about 70–80. The optimal pulse duration is about 75 femtoseconds. It may be, for example a pulsed diode laser, a continuous wave diode laser or a solid state laser. In certain applications, the laser wavelength may be fixed and in others it may be tunable. The input optics 20 preferably includes an input polarizer 22, an input wavelength discriminator 24, an input spatial filter 26 and an input propagation optics 28. The input polarizer 22 could be a brewster angle polarizer, a thin film polarizer, a Glan-air or Glan-Thompson polarizer or other crystal polarizer. The wavelength discriminator may be a color filter, a dielectric film, a holographic transmission filter, or a grating. The input propagation optics 20 could be formed of one or more refractive or reflective optics which, when used in combination, control the divergence or convergence of the beam as it propagates towards the surface.

The second optical source 16 also includes a laser input 30 and associated input optics 32, which may be as described above with respect to the first optical source 12. However, the optics 32 is optimized for the wavelength of the second optical source. The second laser input 30 should also have a pulse in duration of about 50–100 femtoseconds.

Due to their extremely short duration, the femtosecond pulses have very short physical lengths. In order to synchronize the temporal arrival of the pulses, the second optical source 16 includes an optical delay line 33. In its simplest configuration, the optical path from the second optical source to the surface contains optical elements which can vary the distance to the surface. Consequently, the arrival time of the input pulses can be synchronized. The optical delay line 33 may be, for example, a series of mirrors configured in such a way that they add additional propagation distance without changing the input position on the surface to be interrogate. FIG. 2 shows a typical delay line 33. The laser is reflected from a series of four mirrors so that the propagation path is increased by the distance between the first and fourth mirrors. The mirrors are configured so that the propagation directions before the first mirror and after the fourth mirror are collinear and there is no change in propagation direction. By varying the distance between mirrors 1 and 2 (with a corresponding change between mirrors 3 and 4) the optical path to the surface can be varied, changing the arrival time on the surface.

An output wavelength discriminator 34 receives reflections of the first and second laser inputs from the interrogated surface 14. The output wavelength discriminator 34 is substantially non-transmissive at the frequencies of the first laser input and the second laser input, but is substantially transmissive at the sum-frequency of the first laser input and the second laser input. The output wavelength discriminator 34, like the input wavelength discriminators, may comprise a color filter, a dielectric film, a holographic transmission filter, or a grating.

Imaging optics 36 receives an output of the wavelength discriminator 34 and directs the propagation of the output so that a real image is formed after propagation through the imaging optics 36. The imaging optics will be either refractive or reflective optics which, when used in conjunction, act to control the divergence of the light coming from the surface so that a real image is formed.

A position sensitive detector 38 monitors the intensity of the real image at the sum-frequency. The sum-frequency, as a function of surface position, is converted to an electronic signal equivalent to the real image. This may be, for example, a focal plane array, in which local semiconductor pixels absorb the light that falls within a given area and creates an electronic signal proportional to the amount of light incident on it. Utilization of the femtosecond duration laser inputs generates enhanced peak optical powers on the interrogated surface, producing an optimized sum-frequency reflection, resulting in minimized interrogation times.

In a preferred embodiment the first optical source may comprise a femtosecond solid state laser with an output pulse with a maximum of 100 femtoseconds.

The input optics of the first optical source preferably includes a steering apparatus, comprising two mirrors aligned so that that their surface normals are non-coplanar. It also preferably includes a polarization rotator comprising a half-wave plate. The half-wave plate should be optimized for an output wavelength of the input laser. The input optics also preferably uses a linear polarizer that is aligned so that an output wavelength is p or s polarized with the polarization referenced to the surface to be interrogated. A spot shaping apparatus is used, comprising a series of lenses, for creating a controlled spot size on the surface to be interrogated. Finally, a narrow band optical filter is used that passes only an output wavelength or harmonic wavelength of the input laser.

In this preferred embodiment, the second optical source preferably comprises a tunable IR input—an optical parametric oscillator and amplifier tunable output in a band of 1.5–10 microns. The optical parametric oscillator will be designed to produce pulses with a maximum duration of 100 femtosecond duration. A steering apparatus is utilized including two mirrors aligned so that that their surface normals are non-coplanar, with the mirrors' reflectances being optimized for an output wavelength of the infrared laser. A polarization rotator is used that is operative in the infrared range. A linear polarizer is used and is aligned so that an output wavelength is p or s polarized with the polarization referenced to the surface to be interrogated. Again, a spot shaping apparatus is used, including a series of lenses for creating a controlled spot size on the surface to be interrogated, the lenses being transparent in the infrared range. Finally, an optical filter is utilized including a semiconductor crystal having a bandgap that passes infrared but blocks shorter wavelengths. Coatings associated with femtosecond pulses must have designs specifically for femtosecond duration. Due to the short physical dimension, the coatings must have thicknesses small compared to the pulse duration.

The output wavelength discriminator preferably includes an iris; a filter in optical communication with the iris for passing the sum frequency wavelength; and, a linear polarizer in optical communication with the filter, aligned to detect either the p or s polarized sum-frequency wavelength, wherein the polarization is referenced to the surface where the sum-frequency light is generated.

The imaging optics preferably includes a telescope system comprising a plurality of telescope system lenses having coatings optimized for the sum frequency. The position sensitive detector preferably comprises a focal plane array including a silicon detector being electronically gated to only detect output light generated by the input laser pulses. A computer collects and analyzes the electronic data from the position sensitive detector.

Obviously, many modifications and variations of the present invention are possible in light of the above teachings. It is, therefore, to be understood that within the scope of the appended claims, the invention may be practiced otherwise than as specifically described.

What is claimed and desired to be secured by Letters Patent of the United States is:

1. A surface specific optical diagnostic system, comprising:

a) a first optical source for providing a first laser input directable to an area of a surface to be interrogated, said first laser input having a pulse having a duration of about 50–100 femtoseconds;

b) a second optical source for providing a second laser input directable to the surface area to be interrogated, said second laser input having a second pulse having a duration of about 50–100 femtoseconds, said first and second laser inputs being alignable so that their surface areas of optical illumination overlap on said interrogated surface, said second optical source including an optical delay line for temporarily synchronizing said first and second laser inputs;

c) an output wavelength discriminator for receiving reflections of said first and second laser inputs from said interrogated surface, said output wavelength discriminator being substantially non-transmissive at the frequencies of the first laser input and the second laser input, but being substantially transmissive at the sum-frequency of said first laser input and said second laser input;

d) imaging optics for receiving an output of said wavelength discriminator and directing the propagation of the output so that a real image is formed after propagation through said imaging optics; and, e) a position sensitive detector for monitoring the intensity of said real image at said sum-frequency so that the sum-frequency, as a function of surface position, is converted to an electronic signal equivalent to said real image, wherein utilization of the femtosecond duration laser inputs generates enhanced peak optical powers on the interrogated surface, producing an optimized sum-frequency reflection, resulting in minimized interrogation times.

2. The surface specific optical diagnostic system of claim 1, wherein said first optical source comprises a first laser in optical communication with a first input optics.

3. The surface specific optical diagnostic system of claim 2, wherein said first input optics comprises a first input polarizer, a first input wavelength discriminator, a first input spatial filter and first input propagation optics that are in optical communication with each other.

4. The surface specific optical diagnostic system of claim 1, wherein said second optical source comprises a second laser in optical communication with a second input optics, said second input optics being in optical communication with said optical delay line.

5. The surface specific optical diagnostic system of claim 4, wherein said second input optics comprises a second input polarizer, a second input wavelength discriminator, a second input spatial filter and second input propagation optics that are in optical communication with each other.

6. The surface specific optical diagnostic system of claim 1, wherein said first laser input has a pulse range of 70–80 femtoseconds.

7. The surface specific optical diagnostic system of claim 1, wherein said first optical source comprises a diode pumped solid state laser.

8. The surface specific optical diagnostic system of claim 1, wherein said first optical source comprises a Nd:YAG laser operating on the 1.064 micron line.

9. The surface specific optical diagnostic system of claim 1, wherein said first optical source comprises a Nd:YAG laser and a harmonic converter for operation at the second or third harmonic of the laser fundamental output wavelength.

10. The surface specific optical diagnostic system of claim 1, wherein said first optical source comprises a Nd:YAG laser operating on the 1.064 micron line and a has a pulse duration in a range of about 70–80 femtoseconds.

11. The surface specific optical diagnostic system of claim 1, wherein said first optical source comprises a Nd:YAG laser operating on the 1.064 micron line and a has a pulse duration in a range of about 75 femtoseconds.

12. The surface specific optical diagnostic system of claim 1, wherein said first optical source comprises a steering apparatus, comprising two mirrors aligned so that their surface normals are non-coplanar.

13. The surface specific optical diagnostic system of claim 1, wherein said first optical source comprises a laser and a polarization rotator comprising a half-wave plate, said half-wave plate being optimized for an output wavelength of said laser.

14. The surface specific optical diagnostic system of claim 1, wherein said first optical source comprises a laser and linear polarizer, said linear polarizer being aligned so that an output wavelength is p or s polarized with said polarization referenced to said surface to be interrogated.

15. The surface specific optical diagnostic system of claim 1, wherein said first optical source comprises spot shaping apparatus comprising a series of lenses for creating a controlled spot size on said surface to be interrogated.

16. The surface specific optical diagnostic system of claim 1, wherein said first optical source comprises a laser and a narrow band optical filter that passes only an output wavelength or harmonic wavelength of said laser.

17. The surface specific optical diagnostic system of claim 1, wherein said second optical source comprises a tunable IR input.

18. The surface specific optical diagnostic system of claim 1, wherein said second optical source comprises an optical parametric oscillator and amplifier tunable output in a band of 1.5–10 microns.

19. The surface specific optical diagnostic system of claim 1, wherein said second optical source comprises a tunable infrared laser and a steering apparatus comprising two mirrors aligned so that that their surface normals are non-coplanar, with said mirrors' reflectances being optimized for an output wavelength of said infrared laser.

20. The surface specific optical diagnostic system of claim 1, wherein said second optical source comprises a polarization rotator operative in the infrared range.

21. The surface specific optical diagnostic system of claim 1, wherein said second optical source comprises an infrared laser and linear polarizer, said linear polarizer being aligned so that an output wavelength is p or s polarized with said polarization referenced to the surface to be interrogated.

22. The surface specific optical diagnostic system of claim 1, wherein said second optical source comprises spot shaping apparatus comprising a series of lenses for creating a controlled spot size on said surface to be interrogated, said lenses being transparent in the infrared range.

23. The surface specific optical diagnostic system of claim 1, wherein said second optical source comprises an infrared laser and an optical filter, said optical filter comprising a semi-conductor crystal having a bandgap that passes infrared but blocks shorter wavelengths.

24. The surface specific optical diagnostic system of claim 1, wherein said output wavelength discriminator comprises:

an iris;

a filter in optical communication with said iris for passing the sum frequency wavelength; and, a linear polarizer in optical communication with said filter, aligned to transmit either p or s polarized sum-frequency wavelength light, with said polarization referenced to said surface to be interrogated.

25. The surface specific optical diagnostic system of claim 1, wherein said imaging optics comprises a telescope system comprising a plurality of telescope system lenses.

26. The surface specific optical diagnostic system of claim 1, wherein said imaging optics comprises a telescope system comprising a plurality of telescope system lenses having coatings optimized for the sum-frequency.

27. The surface specific optical diagnostic system of claim 1, wherein said position sensitive detector comprises a focal plane array comprising a silicon detector being electronically gated to only detect output light generated by said input laser pulses.

28. A surface specific optical diagnostic system, comprising:

a) a first optical source comprising a Nd:YAG laser operating on the 1.064 micron line for providing a first laser input directable to an area of a surface to be interrogated;

b) a second optical source comprising a tunable IR input for providing a second laser input directable to the surface area to be interrogated, said first and second laser inputs being alignable so that their surface areas of optical illumination overlap on said interrogated surface;

c) an output wavelength discriminator for receiving reflections of said first and second laser inputs from said interrogated surface, said output wavelength discriminator being substantially non-transmissive at the frequencies of the first laser input and the second laser input but being substantially transmissive at the sum-frequency of said first laser input and said second laser input;

d) imaging optics for receiving an output of said wavelength discriminator and directing the propagation of the output so that a real image is formed after propagation through said imaging optics; and, e) a position sensitive detector for monitoring the intensity of said real image at said sum-frequency so that the sum-frequency, as a function of surface position, is converted to an electronic signal equivalent to said real image.

29. A method for diagnosing a surface, comprising the steps of:

a) directing a first laser input from a first optical source to an area of a surface to be interrogated;

b) directing a second laser input from a second optical source to the surface area to be interrogated, said first and second laser inputs being alignable so that their surface areas of optical illumination overlap on said interrogated surface;

c) receiving reflections of said first and second laser inputs from said interrogated surface onto an output wavelength discriminator, said output wavelength discriminator being substantially non-transmissive at the frequencies of the first laser input and the second laser input but substantially transmissive at the sum-frequency of said first laser input and said second laser input;

d) receiving an output of said wavelength discriminator onto imaging optics and directing the propagation of the output so that a real image is formed after propagation through said imaging optics; and, e) monitoring the intensity of said real image at said sum-frequency so that the sum-frequency, as a function of surface position, is converted to an electronic signal equivalent to said real image.

* * * * *